(12) United States Patent
Inoue et al.

(10) Patent No.: US 7,531,165 B2
(45) Date of Patent: May 12, 2009

(54) HAIR COSMETIC, AMINOCARBOXYLIC ACID AMIDE AND METHOD FOR PRODUCING THE SAME

(75) Inventors: Katsuhisa Inoue, Wakayama (JP);
Takeshi Kaharu, Wakayama (JP);
Tohru Katoh, Wakayama (JP)

(73) Assignee: Kao Corporation, Tokyo (JP)

( * ) Notice: Subject to any disclaimer, the term of this patent is extended or adjusted under 35 U.S.C. 154(b) by 872 days.

(21) Appl. No.: 10/997,945

(22) Filed: Nov. 29, 2004

(65) Prior Publication Data

US 2005/0091763 A1    May 5, 2005

Related U.S. Application Data

(63) Continuation of application No. 10/086,873, filed on Mar. 4, 2002, now abandoned.

(30) Foreign Application Priority Data

| Mar. 5, 2001 | (JP) | ................ 2001-060559 |
| Dec. 3, 2001 | (JP) | ................ 2001-368155 |
| Dec. 3, 2001 | (JP) | ................ 2001-368156 |
| Dec. 7, 2001 | (JP) | ................ 2001-374556 |

(51) Int. Cl.
*A61K 8/41* (2006.01)

(52) U.S. Cl. ................. 424/70.1; 424/78.04; 514/645

(58) Field of Classification Search ............... 424/70.1, 424/78.04

See application file for complete search history.

(56) References Cited

U.S. PATENT DOCUMENTS

| 4,639,468 | A | 1/1987 | Roncucci et al. |
| 4,639,668 | A | 1/1987 | Petit et al. |
| 5,573,726 | A | 11/1996 | Dassanayake et al. |
| 5,606,104 | A | 2/1997 | Hatayama et al. |
| 5,888,493 | A | * | 3/1999 | Sawaya | ........... 424/78.04 |
| 6,346,259 | B1 | 2/2002 | Terasaki et al. |

FOREIGN PATENT DOCUMENTS

| DE | 1 165 038 | 3/1964 |
| DE | 1 240 872 | 5/1967 |
| DE | 217 513 | 1/1985 |
| JP | 55-143944 | 9/1980 |
| JP | 5-271035 | 10/1993 |
| JP | 2000-302651 | 10/1995 |
| JP | 8073372 | 3/1996 |
| JP | 09-118606 | 5/1997 |
| JP | 2000-501430 | 9/1998 |
| JP | 5-271036 | 10/2003 |
| WO | WO98/03472 | 1/1998 |
| WO | WO98/40046 | 9/1998 |

OTHER PUBLICATIONS

European Search Report, Nov. 22, 2002, 5pp.
Partial European Search Report, Aug. 22, 2002, 4pp.
Kitzing, et al., CAPLUS 1986:19816, (1985) abstract.
Schmadel, et al., CAPLUS 1967:455389, (1967) abstract.

* cited by examiner

*Primary Examiner*—Gina C. Yu
(74) *Attorney, Agent, or Firm*—Oblon, Spivak, McClelland, Maier & Neustadt, P.C.

(57) ABSTRACT

A hair cosmetic which can impart, to hairs, flexibility, smoothness and oily feeling when the hairs are wetted and smoothness, softness and combing easiness after the hairs are dried are provided, the hair cosmetic comprising an amine represented by the formula (I):

Formula (I)

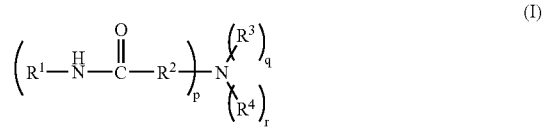

(wherein $R^1$ represents a $C_{8-40}$ alkyl group or alkenyl group or a group represented by the formula $R^5O\text{-}(AO)_n\text{—}C_mH_{2m}$— ($R^5$ represents a $C_{8-40}$ alkyl group or alkenyl group having 8 to 40 carbon atoms, A represents a $C_{2-3}$ alkylene group, n denotes a number from 0 to 30 in average and m denotes an integer of 2 or 3), $R^2$ represents a $C_{1-5}$ alkylene group, $R^3$ represents H, a $C_{1-24}$ alkyl group, alkenyl group or hydroxyalkyl group or a $C_{6-28}$ aryl group or arylalkyl group, $R^4$ represents H, a $C_{1-5}$ alkyl group, alkylene group or hydroxyalkyl group or a $C_{6-28}$ aryl group or arylalkyl group, p denotes an integer from 1 to 3, q and r denote integers from 0 to 2 and p+q+r is equal to 3. Also, the amine (I) can be produced with high selectivity and highly economically by reacting a primary amine with an aminocarboxylic acid to run amidation. An amine represented by the formula (1), its salt or quaternary ammonium salt are also provided:

Formula (1)

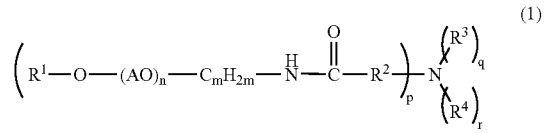

3 Claims, No Drawings

HAIR COSMETIC, AMINOCARBOXYLIC ACID AMIDE AND METHOD FOR PRODUCING THE SAME

TECHNICAL FIELD OF THE INVENTION

The present invention relates to a hair cosmetic which can impart, to hairs, sufficient flexibility, smoothness and further oily feeling when the hairs are wetted and smoothness, softness and combing easiness after the hair are dried and which is environmentally highly safe.

The present invention relates to a method of highly selective production of an aminocarboxylic acid amide which is useful for surfactants or as their intermediates, these surfactants being capable of exhibiting excellent flexibility to fibers and imparting excellent flexibility and smoothness to hairs and being superior in environmental safety as to biodegradation characteristics, toxicity to fishes and to algae and the like.

The invention also relates to a novel amine, its acid salt or its quaternary ammonium salt.

PRIOR ART

It is demanded of hair cosmetics to impart, to hair, sufficient flexibility, smoothness and further oily feeling when the hairs are wetted and smoothness, softness and combing easiness after the hairs are dried. Such a demand currently leads to the use of a quaternary ammonium salt having a long chain alkyl group such as stearyltrimethylammonium chloride and distearyldimethylammonium chloride as a surfactant. However, these compounds insufficiently satisfy working feeling when the hairs are wetted and after the hairs are dried.

JP-A Nos. 5-271035 and 5-271036 and Japanese Patent Application National Publication No. 2000-501430 disclose the use of a salt of an amidoamine which is a tertiary amine type as a base of a hair cosmetic. However, this salt does not satisfy the above requirements and has the drawbacks that it cannot satisfy the compatibility between a feel to the touch, for example, after the hairs are dried and smoothness and oily feeling when the hairs are wetted.

As synthetic examples of an aminocarboxylic acid amide, a method in which an aminocarboxylate is reacted with an. amine and a method in which an amine is reacted with halocarboxylic acid amide are disclosed in JP-A No. 55-143944 and WO98/03472. These methods using an aminocarboxylate or a halocarboxylic acid amide have the problem that a large amount of a reaction solvent is needed when these raw materials and aminocarboxylic acid amide are synthesized and reaction selectivity is low. It is therefore difficult to produce the amide easily.

Various cationic surfactants and acid salts of amine have been used as conditioning agents for fibers and hairs. Performances required at this time are, for example, finish feeling and softness in the case of a fiber softening agent and oily feeling, flexibility and smoothness imparted to hairs since hair is wetted till after the hair is dried in the case of a hair cosmetics.

Based on such functional requirements, quaternary ammonium salts having a long chain alkyl group, such as stearyltrimethylammonium chloride and distearyldimethylammonium chloride are currently used as surfactants.

However, the aforementioned quaternary ammonium salts have the problems concerning environmental safety such as the problem that these salts are not biodegraded but accumulated and adversely affect aquatic organisms such as fishes and algae when residues left after treatment are discharged to the natural world such as rivers. As improved products of the above quaternary ammonium salt, quaternary ammonium salts such as methylbis (hydrogenated beef tallow alkanoyloxyethyl)-2-hydroxyethylammoniummethyl sulfate and dimethylbis(alkanoyloxyethyl)ammonium chloride and acid salts of tertiary amines such as dimethylaminopropyl-octadecaneamide are being placed on the market. However, these compounds are improved in biodegradation characteristics but are not said to be bases which sufficiently satisfy the requirements for flexibility and environmental safety.

JP-A 9-118606 shows a neutralization product with an organic acid and/or an amine of a quaternary ammonium salt having an alkyl or alkenyl having an ester or amide group interrupted for a base material of hair cosmetics. JP-A 2000-302651 shows a quaternary ammonium salt having a glycinamide group for a base material of hair cosmetics.

DISCLOSURE OF THE INVENTION

It is an object of the present invention to provide a hair cosmetic which can impart, to hairs, sufficient flexibility, smoothness and oily feeling when the hairs are wetted and smoothness, softness and combing easiness after the hairs are dried.

The invention provides a hair cosmetic comprising an amine compound (I) having the formula (I) and a process for preparing the amine compound (I).

Then the invention provides an amine compound (1) having the formula (1), an acid salt of (1) and a quaternary ammonium salt of (1). The amine compound (2) having the formula (2) is preferable. Then the invention provides a process for producing the amine compound (1) or (2) and use of the amine compound (1) or (2) for hair cosmetic. These inventions will be explained below. The explanation of hair cosmetic of (I) is applied to that of (1) or (2). The explanation of the production of (I) is applied to that of (1) or (2).

The present invention provides a hair cosmetic comprising an amine (hereinafter referred to as an amine (I)) represented by the formula (I).

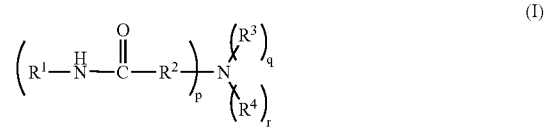
(I)

(wherein $R^1$ represents a straight-chain or branched alkyl group or alkenyl group having 8 to 40 carbon atoms or a group represented by the formula $R^5O\text{-}(AO)_n\text{—}C_mH_{2m}\text{—}$ ($R^5$ represents a straight-chain or branched alkyl group or alkenyl group having 8 to 40 carbon atoms, A represents an alkylene group having 2 to 3 carbon atoms, n denotes a number from 0 to 30 in average and m denotes an integer of 2 or 3, where nAs may be the same or different), $R^2$ represents a straight-chain or branched alkylene group having 1 to 5 carbon atoms, $R^3$ represents a hydrogen atom, a straight-chain or branched alkyl group, alkenyl group or hydroxyalkyl group having 1 to 24 carbon atoms or an aryl group or an arylalkyl group having 6 to 28 carbon atoms, $R^4$ represents a hydrogen atom, a straight-chain or branched alkyl group, alkylene group or hydroxyalkyl group having 1 to 5 carbon atoms or an aryl group or an arylalkyl group having 6 to 28 carbon atoms provided that $R^3$ and $R^4$ may form a ring either independently or in combinations, p denotes an integer from 1 to 3, q and r denote integers from 0 to 2 and p+q+r is equal to 3, provided that $pR^1s$, $pR^2s$, $qR^3s$ and $rR^4S$ may respectively be the same or different.)

Also, it is an object of the present invention to provide a highly economical method for producing an aminocarboxylic acid amide which is useful as a surfactant, which allows fibers to exhibit high flexibility, can impart high flexibility and smoothness to hairs and has high environmental safety as to biodegradation characteristics, toxicity to fishes and to algae and the like or as intermediate of the surfactant, with high selectivity in a high yield without complicated refining operations.

The present invention provides a method for producing an aminocarboxylic acid amide (hereinafter referred to also as an amino carboxylic acid amide (I)) represented by the formula (I):

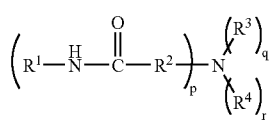

wherein $R^1$, $R^2$, $R^3$, $R^4$, p, q and r respectively have the same meaning as above, comprising reacting a primary amine (hereinafter referred to as a primary amine (II)) represented by the formula (II)

$$R^1-NH_2 \qquad (II)$$

wherein $R^1$ is the same as defined above, with an aminocarboxylic acid (hereinafter referred to as an aminocarboxylic acid (III) represented by the formula (III) to run amidation:

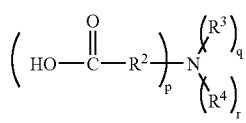

(wherein $R^2$, $R^3$, $R^4$, p, q and r respectively are the same as above.).

It is an object of the present invention to provide a compound which allows fibers to exhibit high flexibility, can impart high flexibility and smoothness to hairs and has high environmental safety as to biodegradation characteristics, toxicity to fishes and to algae and the like.

The present invention provides an amine (hereinafter referred to as an amine (1)) represented by the formula (1) its acid salt or quaternary ammonium salt, especially, a quaternary ammonium salt (hereinafter referred to as a quaternary ammonium salt (2)) represented by the formula (2) and surfactants comprising these compounds:

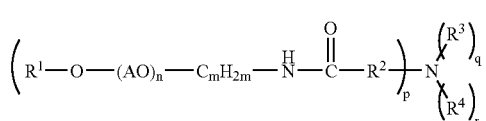

(wherein $R^1$ represents a straight-chain or branched alkyl group or alkenyl group having 8 to 40 carbon atoms, A represents an alkylene group having 2 to 3 carbon atoms, n denotes a number from 0 to 30 in average and m denotes an integer of 2 or 3, $R^2$ represents a straight-chain or branched alkylene group having 1 to 5 carbon atoms, $R^3$ and $R^4$, which are the same or different, respectively represent a hydrogen atom, a straight-chain or branched alkyl group, alkenyl group or hydroxyalkyl group having 1 to 5 carbon atoms or an aryl group or an arylalkyl group having 6 to 28 carbon atoms, provided that $R^3$ and $R^4$ may form a ring either independently or in combinations, p denotes an integer from 1 to 3, q and r denote integers from 0 to 2 and p+q+r is equal to 3, provided that $n^x$pAs, $pR^1$s, pns, pms, $pR^2$s, $qR^3$s and $rR^4$s may respectively be the same or different.)

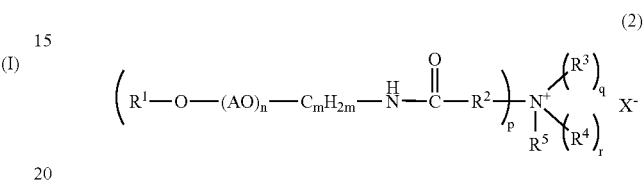

(wherein $R^1$, A, n, m, $R^2$, $R^3$, $R^4$, p, q and r respectively have the same meaning as above, $R^5$ represents a straight-chain or branched alkyl group or hydroxylalkyl group having 1 to 5 carbon atoms and $X^-$ represents an anionic ion group.).

In the formula (1) for the amideamine compound, R1 is not $R^5O$-$(AO)_n$—$C_mH_{2m}$— and R3 does not have 1 to 24 carbon atoms for the alkyl, alkenyl and hydroxyalkyl, but has 1 to 5.
Embodiments of the Invention as to Amine (I) and Hair cosmetic In the amine (I), $R^1$ is preferably a straight-chain or branched alkyl group or alkenyl group having 10 to 28 carbon atoms or a group represented by the formula $R^5O$-$(AO)_n$—$C_mH_{2m}$— wherein $R^5$ is a straight-chain or branched alkyl group or alkenyl group having 10 to 28 carbon atoms and A, n and m have preferably the same meanings as above, more preferably a straight-chain or branched alkyl group or alkenyl group having 12 to 24 carbon atoms or a group represented by the formula $R^5O$-$(AO)_n$—$C_mH_{2m}$— wherein $R^5$ is a straight-chain or branched alkyl group or alkenyl group having 12 to 24 carbon atoms and A, n and m have preferably the same meanings as above and particularly preferably a straight-chain alkyl group having 12 to 24 carbon atoms or a group represented by the formula $R^5O$-$(AO)_n$—$C_mH_{2m}$— wherein $R^5$ is a straight-chain alkyl group having 12 to 24 carbon atoms and A, n and m have the same meanings as above. The aforementioned ns are all preferably 0 to 20 and more preferably 5 or less. $R^2$ is preferably a straight-chain or branched alkylene group having 1 to 3 carbon atoms, more preferably a straight-chain alkylene group having 1 to 3 carbon atoms and most preferably a methylene group. $R^3$ is preferably a straight-chain or branched alkyl group, alkenyl group or hydroxyalkyl group having 1 to 22 carbon atoms or an aryl group or an arylalkyl group having 6 to 28 carbon atoms and more preferably a straight-chain or branched alkyl group or hydroxyalkyl group having 1 to 3 carbon atoms or an aryl group or an arylalkyl group having 6 to 10 carbon atoms. $R^4$ is preferably a straight-chain or branched alkyl group, alkenyl group or hydroxyalkyl group having 1 to 5 carbon atoms or an aryl group or an arylalkyl group having 6 to 28 carbon atoms and more preferably a straight-chain or branched alkyl group or hydroxyalkyl group having 1 to 3 carbon atoms, a phenyl group or a benzyl group. When $R^3$ and $R^4$ are combined with each other to form a ring, the total carbon number of $R^3$ and $R^4$ is preferably 4 to 28 and more preferably 4 to 10 and $R^3$ and $R^4$ respectively are particularly preferably a five-membered ring or a six-membered ring. p is preferably an integer of 1 or 2. q and r respectively are preferably 0 or 1 and particularly a tertiary amine is preferable.

As to a method for producing the amine (I), the amine (I) maybe obtained by a method in which an amine (hereinafter referred to as an amine (II)) represented by the formula (II):

$$R^1\text{—}NH_2 \qquad\qquad\qquad\qquad (II)$$

(wherein $R^1$ has the same meaning as above.)
is reacted with a carboxylic acid halide or its lower alkyl ester or acid halide using a catalyst as the case may be and the reaction product is then reacted with a corresponding amine or by a method in which an amino acid or its derivative is reacted with the amine (II).

The hair cosmetic of the present invention preferably contains at least one acid selected from the group consisting of inorganic acids and organic acids. Examples of the inorganic acids include hydrochloric acid, sulfuric acid and phosphoric acid. As the organic acids, organic acids having 1 to 5 carbon atoms are preferable and acetic acid, glycolic acid, lactic acid, glutamic acid, malic acid and succinic acid are exemplified. Among these acids, hydrochloric acid, sulfuric acid, lactic acid, glutamic acid and malic acid are particularly preferable.

When the hair cosmetic of the present invention is prepared, the amine (I) and the acid may be compounded separately or an acid salt of the amine (I) which is formed in advance may be compounded.

The hair cosmetic of the present invention preferably contains a higher alcohol having 10 to 30 carbon atoms. As higher alcohols to be used in the present invention, higher alcohols containing a straight-chain or branched alkyl group or alkenyl group having 10 to 30 carbon atoms are given, preferably higher alcohols containing a straight-chain alkyl group or alkenyl group having 12 to 26 carbon atoms are given and more preferably higher alcohols such as cetanol, cetyl alcohol, stearyl alcohol, aralkyl alcohol, behenyl alcohol, caranabyl alcohol and ceryl alcohol are given.

The content of the amine (I) in the hair cosmetic of the present invention is preferably 0.1 to 15% by weight and particularly preferably 0.3 to 8% by weight with the view of imparting, to hairs, good feel to the touch and in view of the stability of the product concerning precipitation, solidification, layer separation and the like during storage. Also, the content of the acid is preferably 0.3 to 10 mol equivalents and particularly preferably 0.5 to 5 mol equivalents to the amine (I). Moreover, the content of the higher alcohol is preferably 0.5 to 15% by weight and particularly preferably 1 to 10% by weight with the view of allowing flexibility and wet feeling to be exhibited and in view of the stability of the product.

In the hair cosmetic of the present invention, a part or all of the amine (I) is converted into a salt form upon use by adjusting pH in the composition. The hair cosmetic is preferably used in a pH range from 2 to 8 and particularly from 3 to 6 in view of good feeling of hairs and the stability of the product.

In the hair cosmetic of the present invention, other surfactants such as a cationic surfactant, anionic surfactant, non-ionic surfactant and amphoteric surfactant, silicon, hydrocarbons, lanolin derivatives, higher fatty acid esters, higher fatty acids, oil and fats, glycerol, humectants, cationic polymers, polysaccharides, polypeptides, pearling agents, solvents, liquid crystal forming agents, aromatic sulfonic acids, dyes, perfumes, injection agents, chelating agents, pH regulators, antiseptics and anti-dandruff agents may be compounded properly to the extent that the object of the present invention is not impaired.

The hair cosmetic of the present invention may be made into a desired preparation form such as an aqueous solution, ethanol solution, emulsion, suspension, gel, liquid crystal and air sol.

The hair cosmetic of the present invention may be used for a hair rinse, hair conditioner, hair treatment, hair pack, hair cream, conditioning mousse, hair mousse, hair spray, shampoo and leave-on-treatment.

The hair cosmetic of the present invention allows oily agents, e.g., feeling improvers, to be well-emulsified and the emulsified gel to be highly stable for a long period of time. Also, the hair cosmetic of the present invention can impart, to hairs, good rich feeling, the durability of the rich feeling, flexibility and smoothness when the hairs are wetted and softness and combing easiness after the hairs are dried.

Embodiment of the Invention as to the Production of the Amideamine (I)

The above shown primary amine (II) is used.

Examples of the primary amine (II) include alkyl or alkenylamines such as dodecylamine, tetradecylamine, hexadecylamine, octadecylamine, eicosylamine, docosylamine, tetracosylamine, octadecenylamine, dococenylamine, also, those obtained by converting a long-chain alcohol such as dodecanol, tetradecanol, hexadecanol, octadecanol, eicosanol, docosanol and tetracosanol, ethylene oxide and/or propylene oxide adducts of these alcohols into a cyanoethyl by using acrylonitrile and then by hydrogenating the cyanoethyl by using a catalyst or N-alkylpolyoxyethyleneamine, N-alkylpolyoxypropylene amine and the like which are obtained by halogenating the terminal hydroxyl group of the aforementioned ethylene oxide and/or propylene oxide adduct of the long-chain alcohol and then by reacting the product with ammonia.

In the aminocarboxylic acid (III), $R^2$ is preferably a straight-chain or branched alkylene group having 1 to 3 carbon atoms, more preferably a straight-chain alkylene group having 1 to 3 carbon atoms and particularly preferably a methylene group. $R^3$ is preferably a straight-chain or branched alkyl group, alkenyl group or hydroxyalkyl group having 1 to 22 carbon atoms or an aryl group or an arylalkyl group having 6 to 28 carbon atoms and more preferably a straight-chain or branched alkyl group or hydroxyalkyl group having 1 to 3 carbon atoms or an aryl group or an arylalkyl group having 6 to 10 carbon atoms. $R^4$ is preferably a straight-chain or branched alkyl group, alkenyl group or hydroxyalkyl group having 1 to 5 carbon atoms or an aryl group or an arylalkyl group having 6 to 28 carbon atoms and more preferably a straight-chain or branched alkyl group or hydroxyalkyl group having 1 to 3 carbon atoms, a phenyl group or a benzyl group. When $R^3$ and $R^4$ are combined with each other to form a ring, the total carbon number of $R^3$ and $R^4$ is preferably 4 to 28 and more preferably 4 to 10 and $R^3$ and $R^4$ respectively are particularly preferably a five-membered ring or a six-membered ring. p is preferably an integer of 1 or 2. q and r respectively are preferably 0 or 1 and particularly a tertiary amine is preferable.

Examples of the aminocarboxylic acid (III) include N,N-dimethylglycine, 3-(dimethylamino)propionic acid, 4-(dimethylamino)butanoic acid, N,N-diethylglycine, 3-(diethylamino)propionic acid, 4-(dimethylamino)butanoic acid, N-(2-hydroxyethyl)-N-methylglycine, 3-(N-(2-hydroxyethyl)-N-methylamino)propionic acid, N,N-bis(2-hydroxyethyl)glycine, methyliminodiacetic acid, ethyliminodiacetic acid, nitrilotriacetic acid, pyrrolidinylacetic acid, N-methyl-N-phenylaminoacetic acid and N-methyl-N-tolylaminoacetic acid.

The aminocarboxylic acid (III) may be produced using any method. A corresponding aminocarboxylic acid or its alkali metal salt may be obtained using, for example, a method in which a halocarboxylic acid is reacted with an amine in the presence of a hydroxide of an alkali metal such as NaOH or KOH using, as required, a solvent such as water, a method in which an aldehyde compound such as formalin, sodium cyanide or the like and an amine are used to run a Strecker reaction in the case of a specific aminocarboxylic acid or a method in which an amino alcohol is oxidized using an oxidizing catalyst and an oxidant. An alkali metal salt of aminocarboxylic acid is neutralized by an acid such as sulfuric acid, hydrochloric acid or phosphoric acid, a solvent is distilled as required and the precipitated inorganic salt and the like are removed or decreased to thereby obtain the aminocarboxylic acid.

In the production method of the present invention, almost no effect on reactivity and selectivity is found in the amidation of the aminocarboxylic acid (III) containing an inorganic salt and the aminocarboxylic acid (III) containing no inorganic salt. Specifically, any one of the both may be used. However, high cost facilities and complicated operations are required to obtain the aminocarboxylic acid (II) which contains no inorganic salt at all. Therefore, the aminocarboxylic acid (III) containing an inorganic acid may be used as starting material from an economical point of view and the inorganic salt may be removed at the same time when unreacted starting material is removed after the amidation. Also, the alkali metal salt of the aminocarboxylic acid (II) may be neutralized by the above acid, the amidation reaction may be run as it is and the inorganic salt may be removed after the reaction is finished.

When the amidation according to the present invention is carried out, the aminocarboxylic acid (III) is reacted in an amount of preferably 0.5 to 3 equivalents and more preferably 0.9 to 1.5 equivalents to one equivalent of the primary amine (II).

The reaction temperature in the amidation is preferably 120 to 250° C. and more preferably 140 to 230° C. The reaction time is preferably 1 to 30 hours and more preferably 3 to 20 hours.

Also, in order to restrain the degradation of a hue during amidation, the aminocarboxylic acid (III) and the primary amine (II) may be subjected to reduction treatment using sodium borohydride and an inert gas such as nitrogen and steam may be substituted or introduced during amidation as required.

Further, it is preferable to carry out washing with water and solid-liquid separation for the purpose of removing an unreacted aminocarboxylic acid (III) and impurities such as inorganic acids after the amidation. In the case of washing with water, the amount of water is preferably 5 to 300% by weight and more preferably 10 to 150% by weight based on the amide. The temperature of the washing with water is above the melting point of the amide and preferably 50 to 95° C. The washing with water is carried out preferably around 1 to 3 times. Dehydration after phase separation and isolation makes it possible to remove water left unremoved. In the case of the solid-liquid separation, it may be performed using a known method using a filter press filter, Nutsche type filter or centrifuge.

Also, a deodorizing operation such as steaming may be carried out to decrease the odor of the aminocarboxylic acid amide (I) to be obtained.

Embodiment of the Invention as to Amine (1)

In the formulae (1) and (2), $R^1$ is preferably a straight-chain or branched alkyl group or alkenyl group having 10 to 28 carbon atoms, more preferably a straight-chain or branched alkyl group or alkenyl group having 12 to 24 carbon atoms and particularly preferably a straight-chain alkyl group having 12 to 24 carbon atoms. n represents the number of addition mols of an alkylene oxide and is preferably 0 to 20 in average and more preferably 5 or less. $R^2$ is preferably a straight-chain or branched alkylene group having 1 to 3 carbon atoms, more preferably a straight-chain alkylene group having 1 to 3 carbon atoms and particularly preferably a methylene group.

$R^3$ and $R^4$ respectively are preferably a straight-chain or branched alkyl group or hydroxyalkyl group having 1 to 3 carbon atoms or an aryl group or an arylalkyl group having 6 to 10 carbon atoms and particularly preferably a straight-chain alkyl group or hydroxyalkyl group having 1 to 2 carbon atoms. In the case where $R^3$ and $R^4$ are combined to each other to form a ring, the total number of carbons is preferably 4 to 10 with a five-membered ring or a six-membered ring being particularly preferable. p is preferably an integer of 1 or 2 and particularly preferably 1. $R^5$ is preferably a straight-chain or branched alkyl group or hydroxyalkyl group having 1 to 3 carbon atoms and more preferably a methyl group or an ethyl group.

$X^-$, which represents an anionic ion group, is preferably a halogen ion, a sulfate ion, a carboxylate ion having 1 to 4 carbon atoms, which ion may be substituted with a hydroxyl group or an alkyl sulfate ion having 1 to 4 carbon atoms and more preferably $Cl^-$, $CH_3SO_4^-$ or $CH_3CH_2SO_4^-$.

As the amine (1), for example, the following compounds are given.

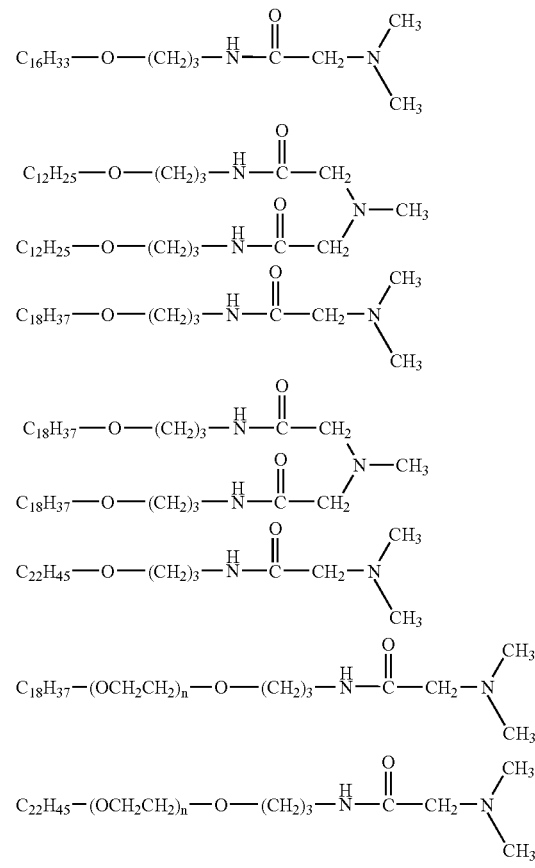

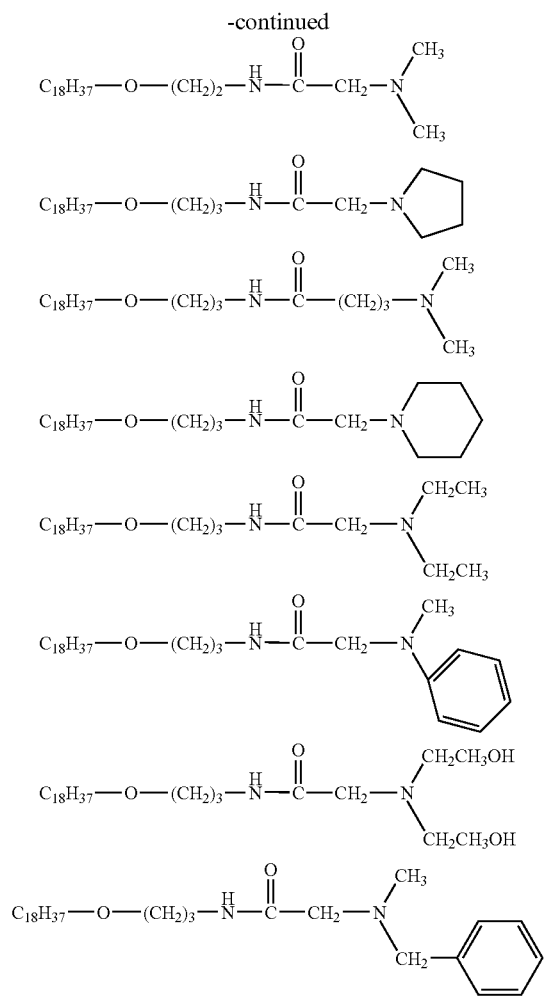
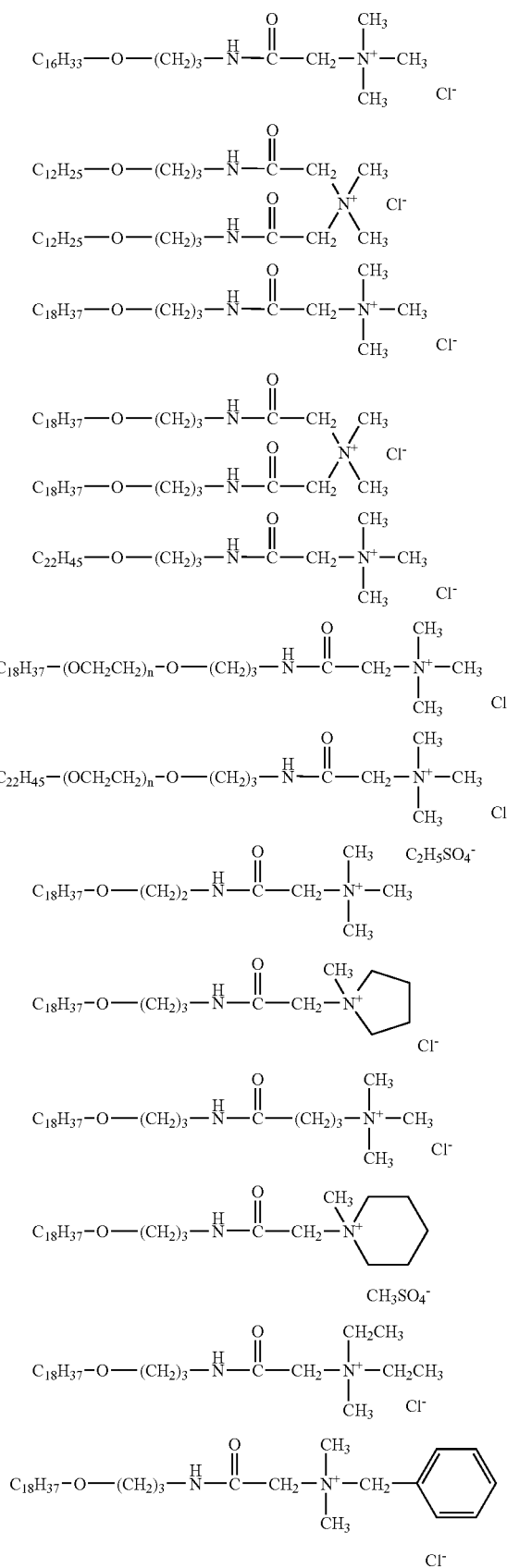

(n=Number of average addition mols 2)
(n=Number of average addition mols 3)

The acid salt of the amine (1) may be obtained neutralizing the amine (1) by using one type selected from inorganic acids and organic acids. Examples of the inorganic acid include hydrochloric acid, sulfuric acid and phosphoric acid. Examples of the organic acid include short-chain acids such as acetic acid and propionic acid; long-chain monocarboxylic acids such as lauric acid, myristic acid, palmitic acid, stearic acid, oleic acid, behenic acid, erucic acid; dicarboxylic acids such as malonic acid, succinic acid, glutaric aid, adipic acid, maleic acid, fumaric acid and phthalic acid; hydroxycarboxylic acids such as glycolic acid, lactic acid, hydroxyacrylic acid, glyceric acid, malic acid, tartaric acid and citric acid; polycarboxylic acids such as polyglutamic acid; acidic amino acids such as glutamic acid and aspartic acid; alkyl sulfates, alkyl sulfonates and alkyl phosphates. Among these compounds, inorganic acids, short-chain monocarboxylic acids, dicarboxylic acids, hydroxycarboxylic acids and acidic amino acids are preferable and hydrochloric acid, sulfuric acid, acetic acid, succinic acid, glycolic acid, lactic acid, malic acid, citric acid and glutamic acid are more preferable.

As the quaternary ammonium salts (2), for example, the following compounds are exemplified.

-continued $$C_{18}H_{37}-O-(CH_2)_3-\overset{H}{N}-\overset{O}{\overset{\|}{C}}-CH_2-\overset{CH_2CH_2OH}{\underset{CH_3}{\overset{|}{N^+}}}-CH_2CH_2OH \quad CH_3SO_4^-$$

The amine (1), its acid salt or quaternary ammonium salt may be produced by the following production methods 1, 2 and 3.

<Production Method 1>

Production Method 1-1

A primary amine (hereinafter referred to as a primary amine (3)) represented by the formula (3) is reacted with an amino compound (hereinafter referred to as an amino compound (4)) represented by the formula (4) to carry out amidation using, as required, a catalyst thereby obtaining the amine (1):

$$R^1-O\text{-}(AO)_n-C_mH_{2m}-NH_2 \quad (3)$$

(wherein $R^1$, A, n and m respectively have the same meaning as above.)

$$\left(R^6-O-\overset{O}{\overset{\|}{C}}-R^2-\right)_p N \overset{(R^3)_q}{\underset{(R^4)_r}{}} \quad (4)$$

(wherein $R^6$ represents a hydrogen atom or a straight-chain or branched alkyl group having 1 to 4 carbon atoms and $R^2$, p, $R^3$, $R^4$, q and r respectively have the same meaning as above.).

Production Method 1-2

A method in which the amine (1, obtained in the production method 1-1 is neutralized by an acid to obtain an acid salt of a corresponding amine.

Production Method 1-3

A method in which the amine (1) obtained in the production method 1-1 is reacted with a quaternary agent (hereinafter referred to as a quaternary agent (5)) represented by the formula (5) and an salt exchange operation is performed according to the need to obtain the quaternary ammonium salt.

$$R^5-X \quad (5)$$

(wherein $R^5$ and X respectively have the same meaning as above.)

<Production Method 2>

Production Method 2-1

A method in which the primary amine (3) is reacted with a haloester (hereinafter referred to as a haloester (6)) represented by the formula (6) using, as required, an alcoholate catalyst:

$$R^7-O-\overset{O}{\overset{\|}{C}}-R^2-Y \quad (6)$$

(wherein $R^7$ represents a straight-chain or branched alkyl group having 1 to 4 carbon atoms, Y represents a halogen atom and $R^2$ has the same meaning as above.)

to carry out amidation, thereby obtaining an haloamide compound (hereinafter referred to as a haloamide compound (7)) represented by the formula (7):

$$R^1-O-(AO)_n-C_mH_{2m}-\overset{H}{N}-\overset{O}{\overset{\|}{C}}-R^2-Y \quad (7)$$

(wherein $R^1$, A, n, m, $R^2$ and Y respectively have the same meaning as above.)

further this haloamide compound and an amine (hereinafter referred to as an amine (8)) represented by the formula (8) are subjected to an amidation reaction by adding, as required, an alkali agent and further, as required, to desalting treatment to obtain the amine (1):

$$(H)_s N \overset{(R^3)_q}{\underset{(R^4)_r}{}} \quad (8)$$

(wherein s=3−q−r and $R^3$, $R^4$, q and r respectively have the same meaning as above.).

Production Method 2-2

A method in which the amine (1) obtained in the production method 2-1 is neutralized using an acid in the same manner as in the production method 1-2 to obtain an acid salt of a corresponding amine.

Production Method 2-3

A method in which the amine (1) obtained in the production method 2-1 is converted into a quaternary compound in the same manner as in the production method 1-3 to obtain a corresponding quaternary ammonium salt.

<Production Method 3>

A method in which a haloamide compound (7) is reacted with an amine (hereinafter referred to as an amine (9)) represented by the formula (9) by adding, as required, an alkali agent and further, as required, the resulting product is subjected to a salt exchange operation to obtain the quaternary ammonium salt:

$$(H)_z N \overset{(R^3)_q}{\underset{R^5(R^4)_r}{}} \quad (9)$$

(wherein z=2−q−r and $R^3$, $R^4$, $R^5$, q and r respectively have the same meaning as above.).

The details of each method of producing the amine (1) and the corresponding acid salt and quaternary ammonium salt will be hereinafter explained.

In the production method 1-1, first using the primary amine (3) and the amino compound (4) in an amount of 0.5 to 3 equivalents and preferably 0.9 to 1.5 equivalents to the primary amine (3), amidation is carried out at 50 to 250° C. and preferably 70 to 230° C. by using, as required, a catalyst over 0.5 to 20 hours to thereby obtain the amine (1).

Given as examples of the primary amine (3) used here are those obtained by converting a long-chain alcohol such as dodecanol, tetradecanol, hexadecanol, octadecanol, eicosanol, docosanol and tetracosanol, ethylene oxide and/or propylene oxide adducts of these alcohols into a cyanoethyl by using acrylonitrile and then by hydrogenating the resulting cyanoethyl by using a catalyst or N-alkylpolyoxyethyleneamine, N-alkylpolyoxypropylene and the like which are obtained by halogenating the terminal OH of the aforementioned ethylene oxide and/or propylene oxide adduct of the long-chain alcohol and then by reacting the product with ammonia.

Examples of the amino compound (4) include N,N-dimethylglycine, 3-(dimethylamino)propionic acid, 4-(dimethylamino)butanoic acid, N,N-diethylglycine, 3-(diethylamino) propionic acid, 4-(diethylamino)butanoic acid, N-(2-hydroxyethyl)-N-methylglycine, 3-(N-(2-hydroxyethyl)-N-methylamino)propionic acid, N,N-bis(2-hydroxyethyl) glycine, methyliminodiacetic acid, ethyliminodiacetic acid, nitrilotriacetic acid, pyrrolidinylacetic acid, N-methyl-N-phenylaminoacetic acid, N-methyl-N-tolylaminoacetic acid and the like and methyl esters, ethyl esters and isopropylesters of these compounds.

As the amidation catalyst, usual alcoholate catalysts may be used in the case of the aforementioned methylester, ethylester and isopropylester and sodium methylate and sodium ethylate are exemplified.

In the production method 1-2, using the amine (1) obtained in the same manner as above and such an acid as shown above in an amount of 0.5 to 3 equivalents and preferably 0.9 to 1.5 equivalents to the amine (1), these components are neutralized at 0 to 100° C. and preferably 20 to 95° C. by using, as required, a solvent such as water, a lower alcohol, e.g., methanol, ethanol or isopropyl alcohol, or acetone to obtain an acid salt of a corresponding amine (1).

In the production method 1-3, using the amine (1) obtained in the same manner as above and the quaternary agent (5) in an amount of 0.5 to 3 equivalent mols and preferably 0.9 to 1.5 equivalent mols to the amine (1), the amine (1) is converted into a quaternary compound at 20 to 140° C. and preferably 40 to 120° C. over 0.5 to 20 hours in no solvent or in a solvent, followed by after-treatment according to a usual method and further, as required, a salt exchange operation is carried out using an ion exchange resin or the like, whereby a quaternary ammonium salt having a necessary counter ion can be obtained.

As examples of the quaternary agent (5) to be used here, lower alkyl halides such as methyl chloride and di-lower alkylsulfuric acids such as dimethylsulfuric acid and diethylsulfuric acid are given.

Examples of the solvent to be used in the reaction for the formation of a quaternary compound include water, methanol, ethanol, isopropyl alcohol and acetone.

In the production method 2-1, first using the primary amine (3) and the haloester (6) in an amount of 0.5 to 3 equivalents and preferably 0.95 to 1.5 equivalents to the primary-amine (3), amidation is carried out at −10 to 100° C. and preferably 0 to 70° C. by using, as required, an alcoholate catalyst and also, as required, a solvent over 1 to 40 hours to obtain a haloamide compound (7).

Next, using an amine (8) in an amount of 0.5 to 20 equivalents and preferably 0.9 to 5 equivalents to the .haloamide compound (7), the haloamide compound (7) is subjected to an amidation reaction at 0 to 120° C. and preferably 10 to 80° C. by adding, as required, an alkali agent and using, as required, a solvent over 1 to 40 hours and then, as required, the resulting product is subjected to desalting treatment, whereby the amine (1) can be obtained.

Examples of the haloester (6) to be used here include methylesters, ethylesters and isopropylesters of monochloroacetic acid, 3-chloropropionic acid, 4-chlorobutylic acid and the like.

Also, examples of the amine (8) include dimethylamine, monomethylamine, ammonia, diethylamine, monoethylamine, diethanolamine, monoethanolamine, methylethylamine, methyl ethanol amine, pyrrolidine, N-methylaniline and methyltolylamine.

Examples of the alcoholate catalyst include sodium methylate and sodium ethylate. Examples of the solvent include methanol, ethanol and isopropyl alcohol. Examples of the alkali agent include NaOH, KOH, sodium carbonate and sodium bicarbonate.

In the production method 2-2, the amine (1) obtained in the above manner is neutralized using an acid in the same manner as in the production method 1-2, whereby the acid salt of the corresponding amine (1) may be obtained.

In the production method 2-3, the amine (1) obtained in the above manner is converted into a quaternary compound in the same manner as in the production method 1-3, whereby the quaternary ammonium salt may be obtained.

In the production method 3, if using the haloamide compound (7) and the amine (9) of 0.5 to 20 equivalents and preferably 0.9 to 5 equivalents to the haloamide compound, the both are reacted with each other at 20 to 140° C. and preferably 30 to 120° C. by adding, as required, an alkali agent and using, as required, a solvent over 0.5 to 20 hours and the resulting product is subjected to desalting treatment according to the need, then to after-treatment according to a usual method and then to a salt exchange operation using an ion exchange resin as required, a quaternary ammonium salt having a necessary counter ion can be obtained.

Examples of the amine (9) to be used here include trimethylamine, triethylamine, triethanolamine, dimethylamine, monomethylamine, diethylamine, monoethylamine, diethanolamine, monoethanolamine, methylethylamine, methyl ethanol amine, pyrrolidine, N-methylaniline and methyltolylamine.

Examples of the solvent include water, methanol, ethanol, isopropyl alcohol and acetone. Examples of the alkali agent include NaOH, KOH, sodium carbonate and sodium bicarbonate.

Each structure of the amine (1) and its acid salt and quaternary ammonium salt according to the present invention can be confirmed by nuclear magnetic resonance spectrum and infrared absorption spectrum.

The amine (1) and its acid salt and quaternary ammonium salt according to the present invention are novel surfactants which impart high flexibility to fibers and high flexibility and smoothness to hairs and are useful as a base having high environmental safety concerning biodegradation characteristics, toxicity to fishes and to algae and the like. Specifically, the amine (1) and its acid salt and quaternary ammonium salt according to the present invention may be used as fiber softeners and hair cosmetics such as hair rinses and hair treatments.

Examples with Regard to Amine (I) and Hair Cosmetics

"%" in examples indicates "% by weight", unless otherwise noted.

Synthetic Example 1

A four-necks-flask equipped with a stirrer, a temperature gage, a dehydrating pipe and a nitrogen-introducing pipe was charged with 801.9 g of Firmine 80 (alkyl primary amine, manufactured by Kao Corporation) and 413.2 g of N,N-dimethylglycineethylester, to which was added 11.6 g of a methanol solution of 28% sodium methylate as a catalyst. The mixture was reacted at 100° C. for 3 hours while the generated ethanol was distilled. Then, 21.3 g of Kyoward 600S (manufactured by Kyowa Chemical Industry Co., Ltd.), followed by adsorbing the catalyst and removing it by filtration to obtain 1036.1 g of an amine A shown in Table 1.

Synthetic Example 2

A four-necks-flask equipped with a stirrer, a temperature gage, a dehydrating pipe and a dropping funnel was charged with 325.6 g of Nissan Amine VBS (alkyl primary amine, manufactured by NOF Corporation), 900 g of methanol and 3.9 g of a methanol solution of 28% sodium methylate as a catalyst. 113.9 g of methyl chloroacetate was added dropwise to the mixture in one hour while the mixture was kept at 15 to 20° C. and the mixture was reacted for 30 hours. After the reaction was completed, the precipitated crystal was filtered and washed with 300 g of methanol, followed by drying to obtain 378.0 g of a corresponding chloroacetamide.

Next, a four-necks-flask equipped with a stirrer, a temperature gage and a cooling tube was charged with 201.0 g of the above chloroacetamide, 219.4 g of diethylamine and 500 g of isopropyl alcohol and the mixture was reacted at 50° C. for 5 hours. After the reaction was completed, 41.7 g of an aqueous 48% sodium hydroxide solution and 100 g of ion-exchange water were added to the reaction mixture. Thereafter, excess diethylamine and solvents were distilled under reduced pressure. Further, the residue was desalted and crystallized using acetone, followed by drying to obtain 201.8 g of an amine B shown in Table 1.

Synthetic Example 3

A four-necks-flask equipped with a stirrer, a temperature gage, a dehydrating pipe and a nitrogen-introducing pipe was charged with 370.7 g of Firmine 20 (alkyl primary amine, manufactured by Kao Corporation) and 147.1 g of N-methyliminodiacetic acid. The mixture was reacted at 180° C. for 10 hours while generated water was distilled. Then, the reaction solution was subjected to crystallization using acetone, followed by drying to obtain 476.4 g of an amine C shown in Table 1.

Synthetic Example 4

The same starting material and conditions as in Synthetic Example 2 were used except that 258.2 g of Firmine 86T (alkyl primary amine, manufactured by Kao Corporation) was used in place of Nissan VBS, to obtain 316.0 g of chloroacetamide.

Next, a four-necks-flask equipped with a stirrer, a temperature gage and a cooling tube was charged with 167.3 g of the above chloroacetamide, 187.8 g of methyl ethanol amine and 500 g of methanol and the mixture was reacted at 35 to 45° C. for 13 hours. After the reaction was completed, 41.7 g of an aqueous 48% sodium hydroxide solution was added to the reaction mixture. Thereafter, excess methyl ethanol amine and solvents were distilled under reduced pressure. Further, the residue was desalted and crystallized using acetone, followed by drying to obtain 328.5 g of an amine D shown in Table 1.

TABLE 1

Amine A

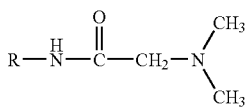

Purity 99.6% (others;alkyl primary uamine, dimethylglycine and the like)

(R: $C_{16}H_{33}/C_{17}H_{35}/C_{18}H_{37}/C_{19}H_{39}/C_{20}H_{41}$ = 4%/1%/93.5%/0.5%/1%)

Amine B

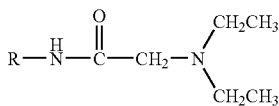

Purity 98.5% (others;alkyl primary amine, diethylglycine, NaCl and the like)

(R: $C_{18}H_{37}/C_{20}H_{41}/C_{22}H_{45}/C_{24}H_{49}$ = 4%/12%/82%/2%)

Amine C

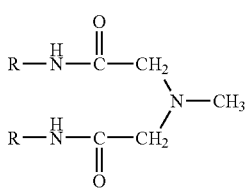

Purity 95.0% (others;monoalkylamide secondary amine, alkyl primary amine, NaCl and the like)

(R: $C_{10}H_{21}/C_{12}H_{25}/C_{14}H_{29}$ = 1%/96%/3%)

Amine D

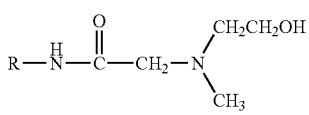

Purity 96.4% (others:alkyl primary amine and the like)

(R: $C_{14}H_{28}/C_{16}H_{33}/C_{18}H_{37}$ = 4%/30%/66%)

Examples 1 to 8 and Comparative Examples 1 and 2

The amines A to D obtained in Synthetic Examples 1 to 4 according to the present invention or Comparative compounds Y (trimethylstearylammonium chloride, manufactured by Tokyo Kasei Kogyo Co., Ltd.) or Comparative compound Z (NIKKOL Amide Amine MPS, manufactured by Nikko Chemicals Co., Ltd.) shown in Table 2 were used to produce hair rinsing agents having the compositions shown in Tables 3 and 4 by a usual method. These hair rinsing agents were evaluated by the following methods. The results are shown in Tables 3 and 4.

TABLE 2

| Comparative compound Y | 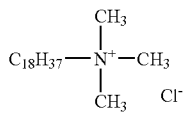 |
|---|---|
| Comparative compound Z | 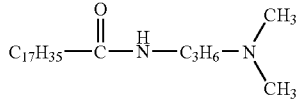 |

<Evaluation Method>

Emulsifiability

The emulsification condition of the hair rinsing agent after it was produced and allowed to stand at 25° C. for 3 hours was evaluated based on the following standard.

○: An emulsified gel is kept stable
Δ: Slightly separated
X: Separated

Storage Stability of Emulsions

The hair rinsing agent was stored at 50° C. for 3 weeks as an accelerated storing test to evaluate the emulsification condition of the gel based on the following standard.

○: An emulsified gel is kept stable
Δ: Slightly separated
X: Separated

Performances of the rinsing agent when it was applied to hairs and hairs were rinsed and after hairs were dried 20 g of the hairs (length: 20 cm, average diameter: 60 μm) of Japanese woman who has not experienced chemical treatment such as cold perm was tied up in a bundle and washed using 5 g of a shampoo. The composition of the shampoo was as follows: sodium polyoxyethylene alkyl (12 carbons) ether sulfate (average addition mols of ethylene oxide: 2.5): 15%, diethanolamide: 3% and water: balance.

After that, 2.0 g of the product of the hair rinsing agent which had been stored at 50° C. for 3 weeks was applied to the hair bundle, which was then rinsed with about –40° C. flowing water for 30 seconds. The rich feeling and its durability, flexibility and smoothness of the hair when the rinsing agent was applied and rinsed and the soft feeling and combing feeling after the hair was dried were functionally evaluated by five expert panelists according to the following standard.

A; Four or more panelists gave an answer to the effect that there was an effect.

B; Three panelists gave an answer to the effect that there was an effect.

C: Two panelists gave an answer to the effect that there was an effect.

D: One or less panelist gave an answer to the effect that there was an effect.

TABLE 3

| | | Example | | | | Comparative example | |
|---|---|---|---|---|---|---|---|
| | | 1 | 2 | 3 | 4 | 1 | 2 |
| Compositions of hair rinsing agents (%) | Amine(I) | A 1.5 | B 1.5 | C 1.5 | D 2.0 | — | — |
| | comparative compound | — | — | — | — | Y 1.0 | Z 1.5 |
| | Hydrochloric acid (molar ratio amine) | — | — | 0.5 | — | — | 0.7 |
| | Lactoc acid(molar ratio amine) | 1.5 | 1.0 | 0.7 | 0.7 | — | — |
| | Cetyl alcohol | 1 | 1 | 1 | 1 | 1 | 1 |
| | Stearyl alkohol | 3 | 2 | 2 | 1 | 2 | 2 |
| | Behenyl alkohol | 1 | 2 | 1 | 3 | 1 | 1 |
| | Liquid paraffin | 2 | 3 | 1 | 3 | 3 | 3 |
| | Dimethylpolysiloxane* | 3 | 2 | 1 | 2 | 3 | 2 |
| | Citric acid(pH regulator) | Proper amount | Proper amount | Proper amount | Proper amount | Proper amount | Proper amount |
| | Purified water | Balance | Balance | Balance | Balance | Balance | Balance |
| | pH | 4 | 5 | 3 | 4.5 | 4 | 6 |
| Result of evaluation | Emulsifiability | ○ | ○ | ○ | ○ | ○ | ○ |
| | Storonge stability of the emulsion | ○ | ○ | ○ | ○ | Δ | Δ |
| when applied and rinsed | Rich feeling | A | A | A | A | D | C |
| | Durability | B | A | B | A | C | B |
| | Flexibility | A | B | C | B | B | C |
| | Smoothness | B | A | A | B | C | B |
| After dried | Soft feeling | A | A | B | A | B | B |
| | Combing feeling | B | B | B | B | C | B |

*KF96A-5000cs manufactured by Shin-Etsu Chemical Co., Ltd.

TABLE 4

|  |  | Example | | | |
| --- | --- | --- | --- | --- | --- |
|  |  | 5 | 6 | 7 | 8 |
| Compositions of hair rinsing agents(%) | Amine (I) | A | A | B | B |
|  |  | 1.7 | 1.5 | 2.0 | 2.0 |
|  | acid(molar ratio amine) | Sulfuric acid | Glutamic acid | Malic acid | Hydrochloric acid |
|  |  | 0.5 | 1.5 | 3 | 1 |
|  | Stearyl alkohol | 4 | 5 | 5 | 6 |
|  | Liquid paraffin | 2 | 2 | 2 | 2 |
|  | Dimethylpolysiloxane | 2 | 2 | 2 | 3 |
|  | Phosphoric acid(pH regulator) | proper amount | proper amount | proper amount | proper amount |
|  | Purified water | balance | balance | balance | balancce |
|  | pH | 3 | 4.5 | 4 | 3.5 |
| Result of evaluation | Emulsifiability | ○ | ○ | ○ | ○ |
|  | Storage stability of the emulsion | ○ | ○ | ○ | ○ |
| when applied and rinsed | Rich feeling | A | A | A | A |
|  | Durability | B | B | A | B |
|  | Flexibility | A | A | B | A |
|  | Smoothness | B | B | A | A |
| After dried | Soft feeling | A | B | A | A |
|  | Combing feeling | B | A | A | B |

*KF96A-5000cs manufactured by Shin-Etsu Chemical Co., Ltd.

Synthetic Example 5

An autoclave equipped with a stirrer and a temperature gage was charged with 256.5 g of Kalcohol 6850 (higher alcohol manufactured by Kao Corporation) and 0.1 g of potassium hydroxide and the mixture was dehydrated at 120° C. under a vacuum of 2.6 kPa for one hour. Then, the mixture was cooled to 60° C. and 58.4 g of acrylonitrile was introduced into the autoclave over one hour, which was then kept as it was for one hour to complete the reaction. Next, 1.9 g of Raney nickel, 0.3 g of sodium hydroxide and 16.1 g of ion exchange water were introduced into the autoclave, which was then reacted for hydrogenation and reduction at 130° C. for 3 hours. Then, the reaction mixture was subjected to filtration to remove the catalyst and refined by distillation to obtain 288.5 g of a corresponding ether primary amine.

Next, a four-necks-flask equipped with a stirrer, a temperature gage, a dehydrating pipe and a nitrogen-introducing pipe was charged with 156.8 g of the above ether primary amine and 61.9 g of N,N-dimethylglycine. The temperature of the mixture was raised to 180° C. The mixture was reacted at the same temperature for 8 hours while generated water was distilled. The reaction mixture was then subjected to crystallization using acetone and dried to obtain 159.5 g of an amine E shown in Table 5.

Synthetic Example 6

The same starting material and conditions as in Synthetic Example 5 were used except that 407.1 g of ethylene oxide (average 3.1 mol) adduct of octadecanol was used in place of Kalcohol 6850 and the distillation-refining was not performed, to obtain 445.6 g of a corresponding ether primary amine.

Next, a four-necks-flask equipped with a stirrer, a temperature gage, dehydrating pipe and a nitrogen-introducing pipe was charged with 232.1 g of the above ether primary amine and 72.2 g of N,N-dimethylglycine and the temperature of the mixture was raised to 190° C. The mixture was reacted at the same temperature for 8 hours while generated water was distilled. The reaction mixture was washed with water to remove excess N,N-dimethylglycine, thereby obtaining 297.1 g of an amine F shown in Table 5.

Synthetic Example 7

The same starting material and conditions as in Synthetic Example 2 were used except that 267.3 g of Firmine 80 (alkyl primary amine, manufactured by Kao Corporation) was used in place of Nissan VBS, to obtain 323.2 g of chloroacetamide.

Next, a four-necks-flask equipped with a stirrer, a temperature gage and a cooling tube was charged with 138.4 g of the above chloroacetamide, 170.69 g of pyrrolidine and 400 g of isopropyl alcohol and the mixture was reacted at 40° C. for 6 hours. After the reaction was completed, 33.1 g of an aqueous 48.3% sodium hydroxide solution and 50 g of ion exchange water were added to the reaction mixture. Thereafter, excess pyrrolidine and solvents were distilled under reduced pressure. Further, the residue was desalted and crystallized using acetone, followed by drying to obtain 108.3 g of an amine G shown in Table 5.

Synthetic Example 8

Next, a four-necks-flask equipped with a stirrer, a temperature gage and a cooling tube was charged with 138.4 g of chloroacetamide obtained in the same manner as in Synthetic Example 7, 257.2 g of N-methylaniline and 395 g of isopropyl alcohol and the mixture was reacted at 60 to 70° C. for 30 hours. After the reaction was completed, 33.1 g of an aqueous 48.3% sodium hydroxide solution and 80 g of ion exchange water were added to the reaction mixture. Thereafter, excess N-methylaniline and solvents were distilled under reduced pressure. Further, the residue was desalted and crystallized using acetone, followed by drying to obtain 132.7 g of an amine H shown in Table 5.

[Table 5]

TABLE 5

Amine E $$R-O-CH_2CH_2CH_2-\overset{H}{N}-\overset{O}{\underset{\|}{C}}-CH_2-N\overset{CH_3}{\underset{CH_3}{\diagdown}}$$

Purity 95% (others; R—OH, R—O—$CH_2CH_2CH_2$—$NH_2$,

TABLE 5-continued

| | |
|---|---|
| | dimethylglicine and the like)<br>(R: $C_{16}H_{33}/C_{18}H_{37}$ = 30%/70%) |
| Amine F | 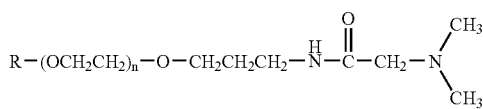 |

Examples 9 to 12 and Comparative Example 3

The amines E to H obtained in Synthetic Examples 5 to 8 according to the present invention and a comparative example Z similar to Comparative Example 2 were used to produce hair rinsing agents having the compositions shown in Table 6 by a usual method. These hair rinsing agents were evaluated in the same manner as in Example 1. The results are shown in Table 6.

TABLE 6

| | | Example | | | | Comprative compound |
|---|---|---|---|---|---|---|
| | | 9 | 10 | 11 | 12 | 3 |
| Compositions of hair rinsing agents (%) | Amine (I) | E<br>1.5 | F<br>1.5 | G<br>1.5 | H<br>1.5 | — |
| | Comparative compound | — | — | — | — | Z<br>1.5 |
| | glutamic acid (molar ratio to amine) | 0.8 | 0.8 | 0.8 | 0.8 | 0.8 |
| | Cetanol*[1] | 4.5 | 4.5 | 4.5 | 4.5 | 4.5 |
| | Isopropyl palmitate | 2 | 2 | 2 | 2 | 2 |
| | Dimethylpolysiloxane*[2] | 2 | 2 | 2 | 2 | 2 |
| | Propylene glycol | 1 | 1 | 1 | 1 | 1 |
| | Phosphoric acid (pHregulator) | Proper amount | Proper amount | Proper amount | Proper amount | Proper amount |
| | Purified water | Balance | Balance | Balance | Balance | Balance |
| | pH | 4.3 | 4.3 | 4.3 | 4.3 | 4.3 |
| Result of evaluation | Emulsifiability | ○ | ○ | ○ | ○ | ○ |
| | Storage stability of the emulsion | ○ | ○ | ○ | ○ | ○ |
| when applied and rinsed | Rich feeling | A | A | B | B | C |
| | Durability | A | A | A | A | C |
| | Flexibility | A | A | A | A | B |
| | Smoothness | A | A | B | B | B |
| After dried | Soft feeling | A | B | A | B | B |
| | Combing feeling | A | A | B | B | B |

*[1]Cetanol is a mixture of cetyl alcohol/stearyl alcohol (ratio by weight 7/3). The same as follows.
*[2]KF96A-5000cs manufactured by Shin-etsu Chemical Co., Ltd.

TABLE 5-continued

| | |
|---|---|
| | Purity 93% (others; R—(OCH$_2$CH$_2$)$_n$—OH, R—(OCH$_2$CH$_2$)$_n$—O—CH$_2$CH$_2$CH$_2$—NH$_2$, dimethylglicine and the like)<br>(R: $C_{18}H_{37}$, n:3.1 mole in average) |
| Amine G | 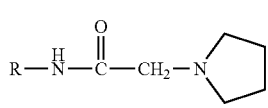 |
| | Purity 97% (others:alkyl primary amine, chloroacetic acid alkylamide, pyrrolidine. NaCl and the like)<br>(R: $C_{16}H_{33}/C_{17}H_{35}/C_{18}H_{37}/C_{19}H_{39}/C_{20}H_{41}$ = 5%/2%/91.5%/0.5%/1%) |
| Amine H | 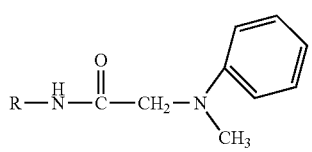 |
| | Purity 96% (others:alkyl primary amine, chloroacetic alkyl amide, methylaniline, NaCl and the like)<br>(R: $C_{16}H_{33}/C_{17}H_{35}/C_{18}H_{37}/C_{19}H_{39}/C_{20}H_{41}$ = 5%/2%/91.5%/0.5%/1%) |

Example 13

A hair rinsing agent having the following composition was produced.

| | |
|---|---|
| Amine A | 3.0% |
| Lactic acid | 2.0% |
| Cetanol | 4.0% |
| Isopropyl palmitate | 2.0% |
| Dimethylpolysiloxane (average molecular weight: 9000) | 1.0% |
| Polyether-modified silicone (KF6015, manufactured by Shin-Etsu Chemical Co., Ltd.) | 2.0% |
| Propylene glycol | 1.5% |
| Aqueous 50% citric acid solution | 0.2% |
| Perfume, methylparaben | Proper amount |
| Purified water | Balance |

(pH: 3.5)

This rinsing agent was emulsified gel-wise and the emulsion had good storage stability. Further, the rinsing agent was superior in rich feeling and its durability, flexibility and smoothness of the hair when the rinsing agent was applied and rinsed and in soft feeling and combing feeling after hairs were dried.

Example 14

A hair treatment agent having the following composition was produced.

| | |
|---|---|
| Amine B | 2.5% |
| Aqueous 35% hydrochloric acid solution | 0.7% |
| Cetanol | 6.5% |
| Dimethylpolysiloxane (average molecular weight: 9000) | 5.0% |
| Polyoxyethylene sorbitan monostearate (number of average addition mols of ethylene oxide: 20) | 0.5% |
| Behenic acid | 0.1% |
| Dipropylene glycol | 6.0% |
| Glycerol | 8.0% |
| Aqueous 50% citric acid solution | 0.2% |
| Perfume, methylparaben | Proper amount |
| Purified water | Balance |

(pH: 3.5)

This hair treatment agent was emulsified gel-wise and the emulsion had good storage stability. Further, the hair treatment agent was superior in rich feeling and its durability, flexibility and smoothness of the hair when the rinsing agent was applied and rinsed and in soft feeling and combing feeling after hairs were dried.

Example 15

A hair treatment agent having the following composition was produced.

| | |
|---|---|
| Amine E | 2.5% |
| 90% lactic acid | 0.9% |
| Cetanol | 4.0% |
| Dimethylpolysiloxane*[1] | 3.0% |
| Amino-modified silicone*[2] | 0.5% |
| Polyoxyethylene sorbitan monostearate (number of average addition mols of ethylene oxide: 20) | 0.5% |
| Liquid paraffin | 2.0% |
| Dipropylene glycol | 3.0% |
| Glycerol | 7.0% |
| Aqueous 50% citric acid solution | 0.2% |
| Hydroxylethyl cellulose*[3] | 0.1% |
| Perfume, methylparaben | Proper amount |
| Purified water | Balance |

(pH: 3.7)
*[1]KF96A-5000 cs, manufactured by Shin-Etsu Chemical Co., Ltd..
*[2]Aminoalkylsilicone emulsion SM8702C, manufactured by Dow Corning Toray Silicone Co., Ltd.
*[3]SE-850, manufactured by Daicel Chemical Industries, Ltd.

This hair treatment agent was emulsified gel-wise and the emulsion had good storage stability. Further, the hair treatment agent was superior in rich feeling and its durability, flexibility and smoothness of the hair when the rinsing agent was applied and rinsed and soft feeling and combing feeling after hairs were dried.

Examples with Regard to the Production of Amine (I)

"%" in examples indicates "% by weight", unless otherwise noted.

Example 16

A four-necks-flask equipped with a stirrer, a temperature gage, a dehydrating pipe and a nitrogen-introducing pipe was charged with 134.1 g of N,N-dimethylglycine and 325.6 g of Nissan Amine VBS (alkyl primary amine, manufactured by NOF Corporation) and the mixture was reacted at 200° C. for 6 hours while nitrogen was introduced into the flask and reaction water was distilled. Thereafter, 102.7 g of water was introduced into the flask after the reaction mixture was cooled to 80° C. The resulting mixture was stirred at 80° C. for 30 minutes and then subjected to phase separation and the water phase was removed. This washing operation was carried out twice to remove unreacted N,N-dimethylglycine and the like. After that, the mixture was dehydrated at 80° C. under a vacuum of 3.9 kPa for one hour. Next, 8.2 g of steam was introduced into the flask at 180° C. under a vacuum of 1.3 kPa in 2 hours to deodorize, thereby obtaining 402.5 g of the target aminocarboxylic acid amide which was a pale yellow solid.

The following structure and composition were confirmed from $^1$H-NMR spectrum, IR spectrum, gas chromatography, atomic absorption spectro photometry and the like.

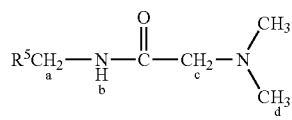

$^1$H-NMR spectrum (CDCl$_3$, internal standard TMS)
a 3.27 ppm (q, 2H)
b 7.13 ppm (1H)
c 2.93 ppm (s, 2H)
d 2.26 ppm (s, 6H)

IR spectrum (KBr tablet)
1648 cm$^{-1}$, 1525 cm$^{-1}$

Purity 98.6%
(others: primary amine: 0.1%, dimethylglycine: 0.1%)

Compositions of an alkyl group represented by R$^5$CH$_2$—
C$_{18}$H$_{37}$/C$_{20}$H$_{41}$/C$_{22}$H$_{45}$/C$_{24}$H$_{49}$=4%/12%/82%/2%

Example 17

The aforementioned amine A was obtained in the same manner as in Example 16.

Example 18

A four-necks-flask equipped with a stirrer, a temperature gage and a cooling tube was charged with 282.4 g of an aqueous 50% N,N-dimethylglycine potassium salt, to which was then added 98% sulfuric acid until the pH was 5.7. Then, the reaction mixture was cooled to 25° C. to remove precipitated potassium sulfate, thereby obtaining 188.3 g of an aqueous 41.1% N,N-dimethylglycine solution containing 2.7% of potassium sulfate.

Next, 151.8g of the aqueous 41.1% N,N-dimethylglycine solution containing 2.7% of potassium sulfate obtained above and 147.0 g of Firmine 80 (alkyl primary amine, manufactured by Kao Corporation) were placed in a flask. The mixture was reacted at 180° C. for 8 hours while nitrogen was introduced into the flask and reaction water was distilled. Thereafter, the reaction mixture was cooled to 70° C. and then 97.0 g of water was introduced and the resulting mixture was stirred at 70° C. for 30 minutes. The separated phase was subjected to a washing operation was carried out to remove unreacted N,N-dimethyl glycine, potassium sulfate and the like. The resulting mixture was dehydrated at 80° C. under a vacuum of 3.9 kPa for one hour to obtain 191.1 g of target aminocarboxylic acid amide which was a pale yellow solid.

The following structure and composition were confirmed from $^1$H-NMR spectrum, IR spectrum, gas chromatography, atomic absorption spectro photometry and the like.

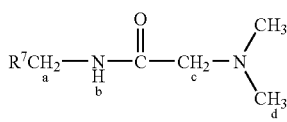

$^1$H-NMR spectrum (CDCl$_3$, internal standard TMS)
   a 3.27 ppm (q, 2H)
   b 7.23 ppm (1H)
   c 2.94 ppm (s, 2H)
   d 2.27 ppm (s, 6H)

IR spectrum (KBr tablet)
   1649 cm$^{-1}$, 1526 cm$^{-1}$

Purity 97.8%
   (Others: primary amine: 0.4%, dimethylglycine: 0.1%, potassium sulfate: 0.1% or less)

Compositions of alkyl groups represented by R$^7$CH$_2$—
   C$_{16}$H$_{33}$/C$_{17}$H$_{35}$/C$_{18}$H$_{37}$/C$_{19}$H$_{39}$/C$_{26}$H$_{41}$=4.5%/2.1%/92.0%/0.5%/0.9%

Example 19

The same four-necks-flask that was used in Example 16 was charged with 168.5 g of N,N-diethylglycine sodium salt and 800.0 g of water and the mixture was neutralized by 111.4 g of an aqueous 36% hydrochloric acid solution. The pH of the resulting solution was 6.5. Next, the solution was concentrated to 70% at 110° C. while nitrogen was blown into the solution. Then, 267.6 g of Firmine 80 (alkyl primary amine, manufactured by Kao Corporation) was introduced into the flask and the mixture was reacted at 170° C. for 12 hours while nitrogen was introduced and reaction water was distilled. Thereafter, the reaction solution was cooled to 80° C. and then 380 g of water was introduced into the flask. The resulting solution was stirred at 80° C. for 30 minutes and an operation of washing the separated phase was carried out twice to remove unreacted N,N-diethylglycine, sodium chloride and the like. The resulting solution was dehydrated at 80° C. under a vacuum of 3.9 kPa for one hour to obtain 369.3 g of target aminocarboxylic acid amide which was a pale yellow solid.

The following structure and composition were confirmed from $^1$H-NMR spectrum, IR spectrum, gas chromatography, atomic absorption spectro photometry and the like.

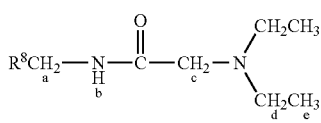

$^1$H-NMR spectrum (CDCl$_3$, internal standard TMS)
   a 3.25 ppm (q, 2H)
   b 7.41 ppm (1H)
   c 3.01 ppm (s, 2H)
   d 2.54 ppm (q, 4H)
   e 1.03 ppm (q, 6H)

IR spectrum (KBr tablet)
   1649 cm$^{-1}$, 1525 cm$^{-1}$

Purity 97.9%
   (others: primary amine: 0.6%, dimethylglycine: 0.2%, sodium chloride: n, 0.1%)

Compositions of an alkyl group represented by R$^8$CH$_2$— C$_{16}$H$_{33}$/C$_{17}$H$_{35}$/C$_{18}$H$_{37}$/C$_{19}$H$_{39}$/C$_{20}$H$_{41}$=5.2%/2.3%/91.3%/0.3%/0.9%

Example 20

An autoclave equipped with a stirrer and a temperature gage was charged with 270.5 g of octadecanol and 0.1 g of potassium hydroxide and the mixture was dehydrated at 120° C. under a vacuum of 2.6 kPa for one hour. Then, the mixture was cooled to 60° C. and 58.4 g of acrylonitrile was introduced into the autoclave over one hour, which was then kept as it was for one hour to complete the reaction. Next, 1.9 g of Raney nickel, 0.3 g of sodium hydroxide and 16.1 g of ion exchange water were introduced into the autoclave, which was then reacted for hydrogenation and reduction at 130° C. for 3 hours. Then, the reaction mixture was subjected to filtration to remove the catalyst, distilled and refined to obtain 294.3 g of a corresponding 3-octadecyloxypropylamine.

Next, a four-necks-flask equipped with a stirrer, a temperature gage, a dehydrating pipe and a nitrogen-introducing pipe was charged with 262.1 g of 3-octadecyloxypropylamine and 220.8 g of an aqueous 41.1% N,N-dimethylglycine solution containing 2.7% of potassium sulfate obtained in the same manner as in Example 3. The temperature of the mixture was raised to 190° C. The mixture was reacted at the same temperature for 7 hours while generated water was distilled and the resulting mixture was cooled to 80° C. Then, the mixture was subjected to a Nutsche type filter to remove unreacted N,N-dimethylglycine, potassium sulfate, and the like to obtain 316.9 g of the target aminocarboxylic acid amide which was a pale yellow solid.

The following structure and composition were confirmed from $^1$H-NMR spectrum, IR spectrum, gas chromatography, atomic absorption spectro photometry and the like.

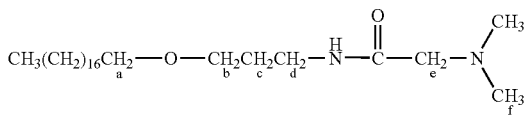

$^1$H-NMR spectrum (CDCl$_3$, internal standard TMS)
   a 3.40 ppm (t, 2H)
   b 3.48 ppm (t, 2H)
   c 1.78 ppm (m, 2H)
   d 3.38 ppm (m, 2H)
   e 2.94 ppm (s, 2H)
   f 2.28 ppm (s, 6H)

IR spectrum (KBr tablet)
   1655 cm$^{-1}$, 1529 cm$^{-1}$, 1122 cm$^{-1}$

Purity 95.3%
   (Others: C$_{18}$H$_{37}$—OH: 2.7%, C$_{18}$H$_{37}$—O—CH$_2$CH$_2$CH$_2$—NH$_2$: 0.8%, dimethylglycine: 0.1%, potassium sulfate: 0.1% or less)

Comparative Example 1

The same four-necks-flask that was used in Example 1 was charged with 325.6 g of Nissan Amine VBS (alkyl primary amine, manufactured by NOF Corporation), 1000 g of methanol as a solvent and 9.6 g of a methanol solution of 28% sodium methylate as a catalyst. 113.9 g of methyl chloroacetate was added dropwise to the mixture in one hour while the mixture was kept at 30 to 40° C. and the resulting mixture was reacted for 6 hours to obtain a reaction product of 2-chloroacetamide. Next, 120.2 g of dimethylamine was introduced into the flask in 3 hours while the mixture was kept at 50 to 60° C. and the resulting mixture was reacted 3 hours. To the reaction solution was added 83.3 g of 48% sodium hydroxide. After that, the solvent methanol was distilled at 80° C., 443 g of water was added to the residue, which was then stirred at 80° C. for 30 minutes to carry out phase separation and the water phase was removed. This washing operation was carried out twice. After that, the mixture was dehydrated at 80° C. under a vacuum of 3.9 kPa for one hour. Next, 8.2 g of steam was introduced into the flask at 180° C. under a vacuum of 1.3 kPa in 2 hours to deodorize, thereby obtaining 390.3 g of an aminocarboxylic acid amide which was a pale brown solid.

It was confirmed from $^1$H-NMR spectrum, IR spectrum, gas chromatography, atomic absorption spectro photometry and the like that this product had the same structure as that of the aminocarboxylic acid amide of Example 1 and the composition of the alkyl group represented by $R^5CH_2$— was also the same. The purity of the product was 82%.

This method requires a large amount of a reaction solvent and therefore the production cost is high. Also, this method has a low reaction selectivity. Therefore it requires a refining operation such as crystallization using an organic solvent if it is intended to obtain a high purity product and also reduced in yield.

Examples with regard to Amine (1)

Example 21

An autoclave equipped with a stirrer and a temperature gage was charged with 270.5 g of octadecanol and 0.1 g of potassium hydroxide and the mixture was dehydrated at 120° C. under a vacuum of 2.6 kPa for one hour. Then, the mixture was cooled to 60° C. and 58.4 g of acrylonitrile was introduced into the autoclave over one hour, which was then kept as it was for one hour to complete the reaction. Next, 1.9 g of Raney nickel, 0.3 g of sodium hydroxide and 16.1 g of ion exchange water were introduced into the autoclave, which was then reacted for hydrogenation and reduction at 130° C. for 3 hours. Then, the reaction mixture was subjected to filtration to remove the catalyst, distilled and refined to obtain 294.3 g of a corresponding 3-octadecyloxypropylamine.

Next, a four-necks-flask equipped with a stirrer; a temperature gage, a dehydrating pipe and a nitrogen-introducing pipe was charged with 262.1 g of 3-octadecyloxypropylamine and 82.5 g of N,N-dimethylglycine. The temperature of the mixture was raised to 180° C. The mixture was reacted at the same temperature for 8 hours while generated water was distilled. Then, the mixture was crystallized using acetone, followed by drying to obtain 297.1 g of the target product (hereinafter referred to as amine i) which was a pale yellow powder.

It was confirmed from $^1$H-NMR spectrum and IR spectrum that the amine i had the following structure.

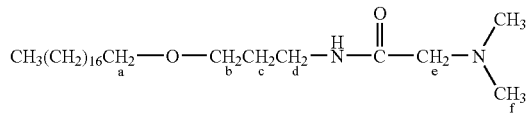

$^1$H-NMR spectrum (CDCl$_3$, internal standard TMS)
a 3.40 ppm (t, 2H)
b 3.48 ppm (t, 2H)
c 1.78 ppm (m, 2H)
d 3.38 ppm (m, 2H)
e 2.94 ppm (s, 2H)
f 2.28 ppm (s, 6H)

IR spectrum (KBr tablet)
1655 cm$^{-1}$, 1529 cm$^{-1}$, 1122 cm$^{-1}$

Example 22

A 2 l beaker was charged with 82.5 g of an amine i obtained in the same method as in Example 21, 36.0 g of an aqueous 50% lactic acid solution and 900 g of ion exchange water and the mixture was stirred at 60° C. for 2 hours to neutralize. Then, the neutralized mixture was freeze-dried to obtain 100.4 g of the target product (lactate of amine i) as a white powder.

It was confirmed from $^1$H-NMR spectrum and IR spectrum that the lactate of amine i had the following structure.

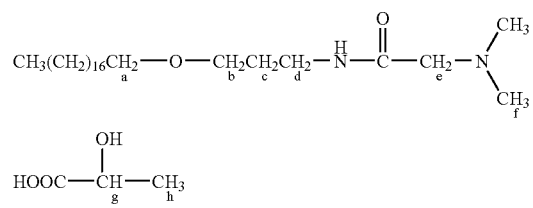

$^1$H-NMR spectrum (CDCl$_3$, internal standard TMS)
a 3.40 ppm (t, 2H)
b 3.49 ppm (t, 2H)
c 1.79 ppm (m, 2H)
d 3.36 ppm (m, 2H)
e 3.31 ppm (s, 2H)
f 2.57 ppm (s, 6H)
g 4.20 ppm (q, 1H)
h 1.41 ppm (w, 3H)

IR spectrum (KBr tablet)
1684 cm$^{-1}$, 1589 cm$^{-1}$, 1122 cm$^{-1}$

Example 23

An autoclave equipped with a stirrer and a temperature gage was charged with 82.5 g of an amine i obtained in the same manner as in Example 21, 12.1 g of methyl chloride and 41.3 g of isopropyl alcohol and the mixture was reacted at 90° C. for 7 hours. Thereafter, the reaction solution was subjected to crystallization using acetone and the resulting crystal was dried to obtain 80.5 g of the target compound (hereinafter referred to as a quaternary ammonium salt i) as a pale yellow powder.

It was confirmed from $^1$H-NMR spectrum and IR spectrum that the quaternary ammonium salt i had the following structure.

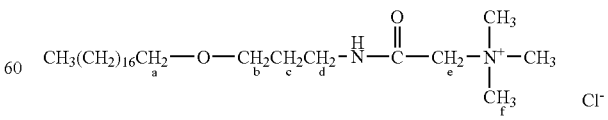

$^1$H-NMR spectrum (CDCl$_3$, internal standard TMS)
a 3.38 ppm (t, 2H)
b 3.45 ppm (t, 2H)
c 1.78 ppm (m, 2H)

d 3.30 ppm (m, 2H)
e 4.17 ppm (s, 2H)
f 3.36 ppm (s, 9H)

IR spectrum (KBr tablet)
1682 cm$^{-1}$, 1560 cm$^{-1}$, 1120 cm$^{-1}$

Example 24

345.3 g of corresponding 3-docosyloxypropylamine was obtained using the same starting material and condition as Example 21, except that 326.6 g of docosanol was used in place of octadecanol.

Next, a four-necks-flask equipped with a stirrer, a temperature gage, a dehydrating pipe and a nitrogen-introducing pipe was charged with 307.0 g of 3-docosyloxypropylamine and 110.2 g of N,N-dimethylglycineethylester, to which was then added 3.1 g of a methanol solution of 28% sodium methylate and the mixture was reacted at 100° C. for 3 hours while generated ethanol was distilled. The reaction solution was subjected to crystallization using acetone and the resulting crystal was dried to obtain 348.8 g of the target compound (hereinafter referred to as an amine ii) as a pale yellow powder.

It was confirmed from $^1$H-NMR spectrum and IR spectrum that the amine ii had the following structure.

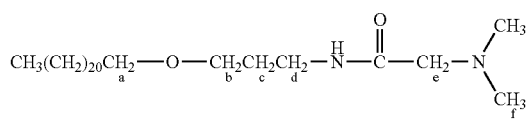

$^1$H-NMR spectrum (CDCl$_3$, internal standard TMS)
a 3.39 ppm (t, 2H)
b 3.47 ppm (t, 2H)
c 1.78 ppm (m, 2H)
d 3.37 ppm (m, 2H)
e 2.94 ppm (s, 2H)
f 2.28 ppm (s, 6H)

IR spectrum (KBr tablet)
1658 cm$^{-1}$, 1531 cm$^{-1}$, 1124 cm$^{-1}$

Example 25

A 2 l beaker was charged with 93.8 g of an amine ii obtained in the same manner as in Example 4, 36.0 g of an aqueous 50% lactic acid solution and 900 g of ion exchange water and the mixture was stirred at 70° C. for 2 hours to neutralize, followed by freeze-drying to obtain 111.8 g of the target compound (lactate of the amine ii) as a white powder.

It was confirmed from $^1$H-NMR spectrum and IR spectrum that the lactate of amine ii had the following structure.

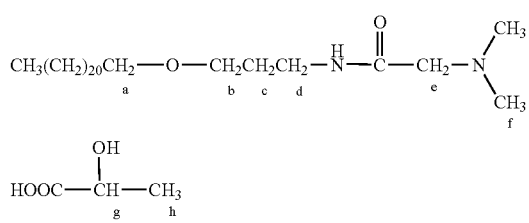

$^1$H-NMR spectrum (CDCl$_3$, internal standard TMS)
a 3.41 ppm (t, 2H)
b 3.48 ppm (t, 2H)
c 1.78 ppm (m, 2H)
d 3.36 ppm (m, 2H)
e 3.30 ppm (s, 2H)
f 2.58 ppm (s, 6H)
g 4.19 ppm (q, 1H)
h 1.41 ppm (w, 3H)

IR spectrum (KBr tablet)
1684 cm$^{-1}$, 1591 cm$^{-1}$, 1121 cm$^{-1}$

Example 26

A four-necks-flask equipped with a stirrer, a temperature gage, a dehydrating pipe and a dropping funnel was charged with 383.69 g of 3-docosyloxypropylamine obtained in the same manner as in Example 24, 1000 g of methanol and 9.6 g of a methanol solution of 28% sodium methylate as a catalyst. 113.9 g of methyl chloroacetate was added to the mixture in one hour while the mixture was kept at 20 to 30° C. and the resulting mixture was reacted for 24 hours. After the reaction was completed, the precipitated crystal was filtered. The crystal was washed with 1000 g of methanol and then dried to obtain 432.6 g of 2-chloro-N-(3-docosyloxypropyl)-acetamide as a white powder.

Next, an autoclave equipped with a stirrer and a temperature gage was charged with 138.1 g of 2-chloro-N-(3-docosyloxypropyl)-acetamide, 21.3 g of trimethylamine and 69.1 g of isopropyl alcohol and the mixture was reacted at 65° C. for 5 hours. After the reaction was completed, the reaction solution was subjected to crystallization using acetone and the resulting crystal was dried to obtain 148.0 g of the target compound (hereinafter referred to as a quaternary ammonium salt ii) as a white powder.

It was confirmed from $^1$H-NMR spectrum and IR spectrum that the quaternary ammonium salt ii had the following structure.

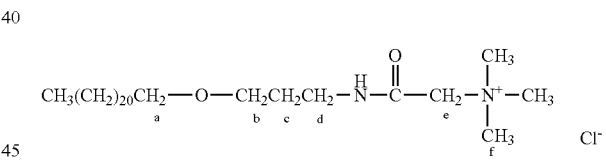

$^1$H-NMR spectrum (CDCl$_3$, internal standard TMS)
a 3.39 ppm (t, 2H)
b 3.45 ppm (t, 2H)
c 1.78 ppm (m, 2H)
d 3.30 ppm (m, 2H)
e 4.17 ppm (s, 2H)
f 3.36 ppm (s, 9H)

IR spectrum (KBr tablet)
1682 cm$^{-1}$, 1561 cm$^{-1}$, 1121 cm$^{-1}$

Example 27

A four-necks-flask equipped with a stirrer, a temperature gage, a dehydrating pipe and a dropping funnel was charged with 327.6 g of 3-octadecyloxypropylamine obtained in the same manner as in Example 21, 900 g of methanol and 3.9 g of a methanol solution of 28% sodium methylate as a catalyst. 113.9 g of methyl chloroacetate was added to the mixture in one hour while the mixture was kept at 15 to 25° C. and the resulting mixture was reacted for 30 hours. After the reaction was completed, the precipitated crystal was filtered. The crystal was washed with 300 g of methanol and then dried to obtain 371.8 g of 2-chloro-N-(3-octadecyloxypropyl)-acetamide as a white powder.

Next, a four-necks-flask equipped with a stirrer, a temperature gage and a cooling tube was charged with 161.6 g of 2-chloro-N-(3-octadecyloxypropyl)-acetamide, 170.69 g of pyrrolidine and 400 g of isopropyl alcohol and the mixture was reacted at 40° C. for 6 hours. After the reaction was completed, 33.1 g of an aqueous 48.3% sodium hydroxide solution and 50 g of ion exchange water were added to the reaction solution. Then, excess pyrrolidine and solvents were distilled under reduced pressure. Further, the resulting solution was desalted and crystallized from acetone. The crystal was dried to obtain 124.8 g of the target product (hereinafter referred to as an amine iii) as a white powder.

It was confirmed from $^1$H-NMR spectrum and IR spectrum that the amine iii had the following structure.

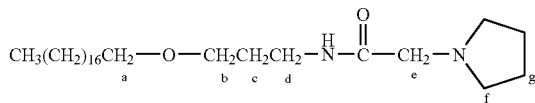

$^1$H-NMR spectrum (CDCl$_3$, internal standard TMS)
 a 3.40 ppm (t, 2H)
 b 3.47 ppm (t, 2H)
 c 1.79 ppm (m, 2H)
 d 3.33 ppm (m, 2H)
 e 3.14 ppm (s, 2H)
 f 2.60 ppm (m, 4H)
 g 1.80 ppm (m, 4H)

IR spectrum (KBr tablet)
 1655 cm$^{-1}$, 1522 cm$^{-1}$, 1122 cm$^{-1}$

Example 28

A four-necks-flask equipped with a stirrer, a temperature gage and a cooling tube was charged with 161.6 g of 2-chloro-N-(3-octadecyloxypropyl)-acetamide obtained in the same manner as in Example 27, 257.2 g of N-methylaniline and 395 g of isopropyl alcohol and the mixture was reacted at 60 to 70° C. for 30 hours. After the reaction was completed, 33.1 g of an aqueous 48.3% sodium hydroxide solution and 80 g of ion exchange water were added to the reaction solution. Then, excess N-methylaniline and solvents were distilled under reduced pressure. Further, the resulting solution was desalted and crystallized using acetone. The crystal was dried to obtain 151.4 g of the target product (hereinafter referred to as an amine iv) as a white powder.

It was confirmed from $^1$H-NMR spectrum and IR spectrum that the amine iv had the following structure.

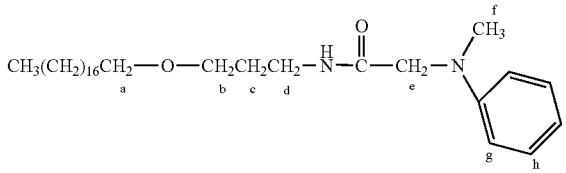

$^1$H-NMR spectrum (CDCl$_3$, internal standard TMS)
 a 3.40 ppm (t, 2H)
 b 3.49 ppm (t, 2H)
 c 1.81 ppm (m, 2H)
 d 3.35 ppm (m, 2H)
 e 3.86 ppm (s, 2H)
 f 3.00 ppm (s, 3H)
 g 6.73 ppm (w, 2H)
 h 7.27 ppm (m, 2H)
 I 6.85 ppm (t, 1H)

IR spectrum (KBr tablet)
 1653 cm$^{-1}$, 1523 cm$^{-1}$, 1122 cm$^{-1}$

Example 29

The same starting material and conditions as in Example 21 were used except that 407.1 g of ethylene oxide (average 3.1 mol) adduct of octadecanol was used in place of octadecanol and the distillation-refining was not performed, to obtain 445.6 g of a corresponding ether primary amine.

Next, a four-necks-flask equipped with a stirrer, a temperature gage, dehydrating pipe and a nitrogen-introducing pipe was charged with 232.1 g of the above ether primary amine and 72.2 g of N,N-dimethylglycine and the temperature of the mixture was raised to 190° C. The mixture was reacted at the same temperature for 8 hours while generated water was distilled. The reaction mixture was washed with water to remove excess N,N-dimethylglycine, thereby obtaining 297.1 g of the target compound (hereinafter referred to as an amine v) as a pale yellow solid.

It was confirmed from $^1$H-NMR spectrum and IR spectrum that the amine v had the following structure.

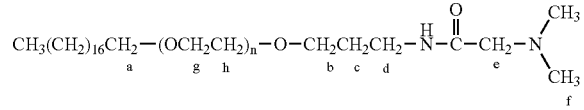

$^1$H-NMR spectrum (CDCl$_3$, internal standard TMS)
 a 3.40 ppm (t, 2H)
 b 3.48 ppm (t, 2H)
 c 1.79 ppm (m, 2H)
 d 3.38 ppm (m, 2H)
 e 2.94 ppm (s, 2H)
 f 2.27 ppm (s, 6H)
 g, h 3.50 to 3.65 ppm (12. 4H)

IR spectrum (KBr tablet)
 1655 cm$^{-1}$, 1527 cm$^{-1}$, 1120 cm$^{-1}$

Examples 30 to 31, Comparative Example 1

The amines i and v obtained in Examples 21 and 29 and a comparative amine (NIKKOL Amide Amine MPS, manufactured by Nikko Chemicals Co., Ltd.) represented by the formula (10) were used to produce hair rinsing agents having the compositions shown in Table 7 by a usual method. These hair rinsing agents were evaluated by the following methods. The results are shown in Table 7.

(10)

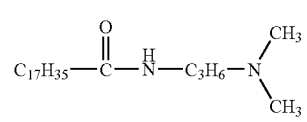

<Evaluation Method>

Emulsifiability

The emulsification condition of the hair rinsing agent after it was produced and allowed to stand at ambient temperature (25° C.) for 3 hours was evaluated based on the following standard.

B; Three panelists gave an answer to the effect that there was an effect.

C: Two panelists gave an answer to the effect that there was an effect.

D: One or less panelist gave an answer to the effect that there was an effect.

TABLE 7

|  |  | Example | | Comparative example |
|---|---|---|---|---|
|  |  | 10 | 11 | 1 |
| Compositions of hair rinsing agents (%) | Amine | Amine i 1.5 | Amine v 1.5 | Comparative Amine 1.5 |
|  | Glutamic acid (molar ratio to amine) | 0.8 | 0.8 | 0.8 |
|  | Cetanol*1 | 4.5 | 4.5 | 4.5 |
|  | Isopropyl palmitate | 2 | 2 | 2 |
|  | Dimethylpolysiloxane*2 | 2 | 2 | 2 |
|  | plopylene glycol | 1 | 1 | 1 |
|  | Citric acid(pH regulator) | proper amount | proper amount | proper amount |
|  | Purified water | balance | balance | balance |
|  | pH | 4.3 | 4.3 | 4.3 |
| Result of evaluation | emulsification | ○ | ○ | ○ |
|  | Storage stability of the emulsion | ○ | ○ | ○ |
| when applied and rinsed | rich feeling | A | A | C |
|  | durability | A | A | C |
|  | Softness | A | A | B |
|  | Smoothness | A | A | B |
| After dried | Softness | A | B | B |
|  | Combing feeling | A | A | B |

*1Cetanol is a mixture of cetyl alcohol/stearyl alkohol(ratio by weight: 7/3)
*2KF96A-5000cs manufactured by Shin-Etsu Chemical Co., Ltd ○: An emulsified gel is kept stable
Δ: Slightly separated
X: Separated Storage Stability of Emulsions The hair rinsing agent was stored at 50° C. for 3 weeks as an accelerated storing test to evaluate the emulsification condition of the gel based on the following standard.
○: An emulsified gel is kept stable
Δ: Slightly separated
X: Separated Performances of the rinsing agent when it was applied to hairs and hairs were rinsed and after hairs were dried 20 g of the hairs (length: 20 cm, average diameter: 60 μm) of Japanese woman who had not experienced chemical treatment such as cold perm was tied up in a bundle and washed using 5 g of a shampoo. The composition of the shampoo was as follows: sodium polyoxyethylene alkyl (12 carbons) ether sulfate (average addition mols of ethylene oxide: 2.5): 15%, diethanolamide: 3% and water: balance.

After that, 2.0 g of the product of the hair rinsing agent which had been stored at 50° C. for 3 weeks was uniformly applied to the hair bundle, which was then rinsed with about ~40° C. flowing water for 30 seconds. The rich feeling and its durability, flexibility and smoothness of the hair when the rinsing agent was applied and rinsed and the soft feeling and combing feeling after the hair was dried were functionally evaluated by five expert panelists according to the following standard.

A; Four or more panelists gave an answer to the effect that there was an effect.

The invention claimed is:

1. A hair cosmetic comprising an amine compound of formula (I):

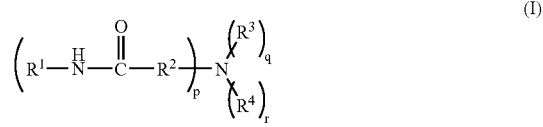

wherein, $R^1$ represents a group represented by the formula $R^5O\text{-}(AO)_n\text{-}C_mH_{2m}\text{-}$ where $R^5$ represents a straight-chain or branched alkyl or alkenyl group having 8 to 40 carbon atoms, A represents an alkylene group having 2 to 3 carbon atoms, n denotes 0 and m denotes 3, where nA's may be the same as or different from one another $R^2$ represents a straight-chain or branched alkylene group having 1 to 5 carbon atoms, $R^3$ represents a hydrogen atom, a straight-chain or branched alkyl, alkenyl or hydroxyalkyl group having 1 to 24 carbon atoms or an aryl or arylalkyl group having 6 to 28 carbon atoms, $R^4$ represents a hydrogen atom, a straight-chain or branched alkyl, alkylene or hydroxyalkyl group having 1 to 5 carbon atoms or an aryl or arylalkyl group having 6 to 28 carbon atoms, $R^3$ and $R^4$ form a ring either independently or in combination, p denotes an integer from 1 to 3, q and r denote an integer from 0 to 2 and p+q+r is equal to 3, that pR$^{1'}$s, pR$^{2'}$s, qR$^{3'}$s and rR$^{4'}$s may be the same as or different from one another; and an alcohol having 10 to 30 carbon atoms.

2. The hair cosmetic of claim 1, wherein in the formula (I), R$^1$ represents a group represented by the formula R$^5$O-(AO)$_n$—C$_m$H$_{2m}$— where R$^5$ represents a straight-chain or branched alkyl or alkenyl group having 12 to 24 carbon atoms, A, n and m represent the same meaning as above R$^2$ represents a straight-chain alkylene group having 1 to 3 carbon atoms, R$^3$ and R$^4$ represent a straight-chain or branched alkyl or hydroxyalkyl group having 1 to 3 carbon atoms or an aryl or arylalkyl group having 6 to 28 carbon atoms (R$^3$ and R$^4$ may form a ring either independently or in combination), p is 1 or 2 and q and r are 0 or 1.

3. A hair cosmetic comprising:

an amine compound of formula (I):

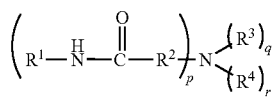

(I)

wherein,

R$^1$ represents a group represented by the formula R$^5$O-(AO)$_n$—C$_m$H$_{2m}$— where R$^5$ represents a straight-chain or branched alkyl or alkenyl group having 8 to 40 carbon atoms. A represents an alkylene group having 2 to 3 carbon atoms, n denotes 0 and m denotes 3, where nA's may be the same as or different from one another R$^2$ represents a straight-chain or branched alkylene group having 1 to 5 carbon atoms, R$^3$ represents a hydrogen atom, a straight-chain or branched alkyl, alkenyl or hydroxyalkyl group having 1 to 24 carbon atoms or an aryl or arylalkyl group having 6 to 28 carbon atoms, R$^4$ represents a hydrogen atom, a straight-chain or branched alkyl, alkylene or hydroxyalkyl group having 1 to 5 carbon atoms or an aryl or arylalkyl group having 6 to 28 carbon atoms, R$^3$ and R$^4$ may form a ring either independently or in combination, p denotes an integer from 1 to 3, q and r denote an integer from 0 to 2 and p+q+r is equal to 3, that pR$^{1'}$s, pR$^{2'}$s, qR$^{3'}$s and rR$^{4'}$s may be the same as or different from one another; and i) at least one acid selected from the group consisting of inorganic acids and organic acids; and ii) an alcohol having 10 to 30 carbon atoms, wherein the content of the amine compound (I) is 0.1 to 15% by weight, the content of the acid is 0.3 to 10 mol equivalents to the amine (I) and the content of alcohol having 10 to 30 carbon atoms is 0.5 to 15% by weight.

* * * * *

UNITED STATES PATENT AND TRADEMARK OFFICE
CERTIFICATE OF CORRECTION

PATENT NO. : 7,531,165 B2 Page 1 of 1
APPLICATION NO. : 10/997945
DATED : May 12, 2009
INVENTOR(S) : Inoue et al.

It is certified that error appears in the above-identified patent and that said Letters Patent is hereby corrected as shown below:

On the title page, Item (45) and the Notice information should read as follows:

--(45) **Date of Patent: * May 12, 2009**

(*) Notice: Subject to any disclaimer, the term of this patent is extended or adjusted under 35 U.S.C. 154(b) by 872 days.

This patent is subject to a terminal disclaimer.--

Signed and Sealed this

Thirtieth Day of June, 2009

JOHN DOLL
*Acting Director of the United States Patent and Trademark Office*